United States Patent
Steen et al.

(10) Patent No.: US 10,485,699 B2
(45) Date of Patent: Nov. 26, 2019

(54) SYSTEMS AND METHODS FOR TRANSVERSE PHACOEMULSIFICATION

(75) Inventors: Mark Steen, Santa Ana, CA (US); Rob Raney, Laguna Beach, CA (US); John Muri, Aliso Viejo, CA (US); George Bromfield, Santa Ana, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 913 days.

(21) Appl. No.: 11/753,554

(22) Filed: May 24, 2007

(65) Prior Publication Data
US 2008/0294087 A1    Nov. 27, 2008

(51) Int. Cl.
*A61F 9/007*    (2006.01)
*A61B 17/32*    (2006.01)

(52) U.S. Cl.
CPC ............. *A61F 9/00745* (2013.01); *A61B 2017/320098* (2017.08)

(58) Field of Classification Search
CPC ..... A61F 9/00745; A61B 2017/320096; A61B 2017/320098; A61B 17/320068
USPC ............. 606/169, 170, 107, 166, 1; 604/22; 175/56; 600/565
See application file for complete search history.

(56) References Cited

U.S. PATENT DOCUMENTS

| | | | |
|---|---|---|---|
| 1,848,024 A | 3/1932 | Owen | |
| 2,123,781 A | 7/1938 | Huber | |
| 2,990,616 A * | 7/1961 | Kuris | A61C 1/07 228/1.1 |
| 3,076,904 A | 2/1963 | Klesattel et al. | |
| 3,116,697 A | 1/1964 | Bilichniansky | |
| 3,439,680 A | 4/1969 | Thomas, Jr. | |
| 3,526,219 A * | 9/1970 | Balamuth Lewis | 600/565 |
| 3,781,142 A | 12/1973 | Zweig | |
| 3,857,387 A | 12/1974 | Shock | |
| 4,017,828 A | 4/1977 | Watanabe et al. | |
| 4,037,491 A | 7/1977 | Newbold | |
| 4,189,286 A | 2/1980 | Murry et al. | |
| 4,193,004 A | 3/1980 | Lobdell et al. | |
| 4,276,023 A | 6/1981 | Phillips et al. | |

(Continued)

FOREIGN PATENT DOCUMENTS

| | | |
|---|---|---|
| AU | 2006235983 A1 | 5/2007 |
| DE | 3826414 A1 | 2/1989 |

(Continued)

OTHER PUBLICATIONS

Boyd, "Preparing for the Transition" in: The Art and the Science of Cataract Surgery, Chapter 7, 2001, pp. 93-133.
Definition of "Parameter", Retrieved from the Internet: Feb. 12, 2007.

(Continued)

*Primary Examiner* — Katrina M Stransky
(74) *Attorney, Agent, or Firm* — Johnson & Johnson Surgical Vision, Inc.

(57) ABSTRACT

The invention is generally directed to phacoemulsification systems and methods, and more particularly to systems and methods for providing transverse phacoemulsification. In accordance with one embodiment, a phacoemulsification system is provided having a handpiece with a needle, wherein the phacoemulsification system is configured to vibrate the distal end of the needle in both an effective transverse direction and an effective longitudinal direction when power, having a single effective operating frequency is applied to the handpiece.

26 Claims, 10 Drawing Sheets

(56) References Cited

U.S. PATENT DOCUMENTS

| | | | |
|---|---|---|---|
| 4,537,561 A | 8/1985 | Xanthopoulos | |
| 4,564,342 A | 1/1986 | Weber et al. | |
| 4,590,934 A | 5/1986 | Malis et al. | |
| 4,662,829 A | 5/1987 | Nehring | |
| 4,665,621 A | 5/1987 | Ackerman et al. | |
| 4,706,687 A | 11/1987 | Rogers et al. | |
| 4,757,814 A | 7/1988 | Wang et al. | |
| 4,758,220 A | 7/1988 | Sundblom et al. | |
| 4,772,263 A | 9/1988 | Dorman et al. | |
| 4,773,897 A | 9/1988 | Scheller et al. | |
| 4,818,186 A | 4/1989 | Pastrone et al. | |
| 4,837,857 A | 6/1989 | Scheller et al. | |
| 4,920,336 A | 4/1990 | Meijer | |
| 4,921,477 A | 5/1990 | Davis | |
| 4,933,843 A | 6/1990 | Scheller et al. | |
| 4,941,518 A | 7/1990 | Williams et al. | |
| 4,954,960 A | 9/1990 | Lo et al. | |
| 4,961,424 A * | 10/1990 | Kubota | A61B 17/22012 601/2 |
| 4,965,417 A | 10/1990 | Massie | |
| 4,983,901 A | 1/1991 | Lehmer | |
| 4,998,972 A | 3/1991 | Chin et al. | |
| 5,006,110 A | 4/1991 | Garrison et al. | |
| 5,020,535 A | 6/1991 | Parker et al. | |
| 5,026,387 A | 6/1991 | Thomas | |
| 5,032,939 A | 7/1991 | Mihara et al. | |
| 5,039,973 A | 8/1991 | Carballo | |
| 5,091,656 A | 2/1992 | Gahn | |
| 5,108,367 A | 4/1992 | Epstein et al. | |
| 5,110,270 A | 5/1992 | Morrick | |
| 5,116,343 A | 5/1992 | Ams et al. | |
| 5,125,891 A | 6/1992 | Hossain et al. | |
| 5,160,317 A | 11/1992 | Costin | |
| 5,195,960 A | 3/1993 | Hossain et al. | |
| 5,195,961 A | 3/1993 | Takahashi et al. | |
| 5,195,971 A | 3/1993 | Sirhan | |
| 5,230,614 A | 7/1993 | Zanger et al. | |
| 5,242,404 A | 9/1993 | Conley et al. | |
| 5,249,121 A | 9/1993 | Baum et al. | |
| 5,268,624 A | 12/1993 | Zanger | |
| 5,271,379 A | 12/1993 | Phan et al. | |
| 5,282,787 A | 2/1994 | Wortrich | |
| 5,323,543 A | 6/1994 | Steen et al. | |
| 5,342,293 A | 8/1994 | Zanger | |
| 5,350,357 A | 9/1994 | Kamen et al. | |
| 5,351,676 A | 10/1994 | Putman | |
| 5,388,569 A | 2/1995 | Kepley | |
| 5,454,783 A | 10/1995 | Grieshaber et al. | |
| 5,464,391 A | 11/1995 | Devale | |
| 5,470,211 A | 11/1995 | Knott et al. | |
| 5,470,312 A | 11/1995 | Zanger et al. | |
| 5,499,969 A | 3/1996 | Beuchat et al. | |
| 5,520,652 A | 5/1996 | Peterson | |
| 5,533,976 A | 7/1996 | Zaleski et al. | |
| 5,549,461 A | 8/1996 | Newland | |
| 5,554,894 A | 9/1996 | Sepielli | |
| 5,561,575 A | 10/1996 | Eways | |
| 5,569,188 A | 10/1996 | MacKool | |
| 5,580,347 A | 12/1996 | Reimels | |
| 5,591,127 A | 1/1997 | Barwick et al. | |
| 5,653,887 A | 8/1997 | Wahl et al. | |
| 5,657,000 A | 8/1997 | Ellingboe | |
| 5,676,530 A | 10/1997 | Nazarifar | |
| 5,676,649 A * | 10/1997 | Boukhny | A61F 9/00745 604/22 |
| 5,676,650 A | 10/1997 | Grieshaber et al. | |
| 5,693,020 A | 12/1997 | Rauh | |
| 5,697,898 A | 12/1997 | Devine | |
| 5,697,910 A | 12/1997 | Cole et al. | |
| 5,700,240 A | 12/1997 | Barwick, Jr. et al. | |
| 5,724,264 A | 3/1998 | Rosenberg et al. | |
| 5,728,130 A | 3/1998 | Ishikawa et al. | |
| 5,733,256 A | 3/1998 | Costin | |
| 5,745,647 A | 4/1998 | Krause | |
| 5,746,713 A | 5/1998 | Hood et al. | |
| 5,747,824 A | 5/1998 | Jung et al. | |
| 5,777,602 A | 7/1998 | Schaller et al. | |
| 5,805,998 A | 9/1998 | Kodama | |
| 5,807,075 A | 9/1998 | Jacobsen et al. | |
| 5,810,766 A | 9/1998 | Barnitz et al. | |
| 5,830,176 A | 11/1998 | MacKool | |
| 5,843,109 A | 12/1998 | Mehta et al. | |
| 5,859,642 A | 1/1999 | Jones | |
| 5,871,492 A | 2/1999 | Sorensen | |
| 5,879,298 A | 3/1999 | Drobnitzky et al. | |
| 5,883,615 A | 3/1999 | Fago et al. | |
| 5,899,674 A | 5/1999 | Jung et al. | |
| 5,928,257 A | 7/1999 | Kablik et al. | |
| 5,938,655 A | 8/1999 | Bisch et al. | |
| 5,983,749 A | 11/1999 | Holtorf | |
| 6,002,484 A | 12/1999 | Rozema et al. | |
| 6,024,428 A | 2/2000 | Uchikata | |
| 6,028,387 A | 2/2000 | Boukhny | |
| 6,062,829 A | 5/2000 | Ognier | |
| 6,077,285 A * | 6/2000 | Boukhny | 606/169 |
| 6,086,598 A | 7/2000 | Appelbaum et al. | |
| 6,109,895 A | 8/2000 | Ray et al. | |
| 6,117,126 A | 9/2000 | Appelbaum et al. | |
| 6,139,320 A | 10/2000 | Hahn | |
| 6,150,623 A | 11/2000 | Chen | |
| 6,159,175 A * | 12/2000 | Strukel | A61M 1/0035 604/118 |
| 6,179,829 B1 | 1/2001 | Bisch | |
| 6,200,287 B1 | 3/2001 | Keller et al. | |
| 6,219,032 B1 | 4/2001 | Rosenberg et al. | |
| 6,251,113 B1 | 6/2001 | Appelbaum et al. | |
| 6,260,434 B1 | 7/2001 | Holtorf | |
| 6,360,630 B2 | 3/2002 | Holtorf | |
| 6,368,269 B1 | 4/2002 | Lane | |
| 6,411,062 B1 | 6/2002 | Baranowski et al. | |
| 6,424,124 B2 | 7/2002 | Ichihara et al. | |
| 6,436,072 B1 | 8/2002 | Kullas et al. | |
| 6,452,120 B1 | 9/2002 | Chen | |
| 6,452,123 B1 | 9/2002 | Chen | |
| 6,491,661 B1 | 12/2002 | Boukhny et al. | |
| 6,511,454 B1 | 1/2003 | Nakao et al. | |
| 6,537,445 B2 | 3/2003 | Muller | |
| 6,595,948 B2 | 7/2003 | Suzuki et al. | |
| 6,632,214 B2 | 10/2003 | Morgan et al. | |
| 6,674,030 B2 | 1/2004 | Chen et al. | |
| 6,830,555 B2 | 12/2004 | Rockley et al. | |
| 6,852,092 B2 | 2/2005 | Kadziauskas et al. | |
| 6,862,951 B2 | 3/2005 | Peterson et al. | |
| 6,908,451 B2 | 6/2005 | Brody et al. | |
| 6,962,488 B2 | 11/2005 | Davis et al. | |
| 6,962,581 B2 | 11/2005 | Thoe | |
| 6,986,753 B2 | 1/2006 | Bui | |
| 7,011,761 B2 | 3/2006 | Muller | |
| 7,012,203 B2 | 3/2006 | Hanson et al. | |
| 7,070,578 B2 | 7/2006 | Leukanech et al. | |
| 7,073,083 B2 | 7/2006 | Litwin, Jr. et al. | |
| 7,087,049 B2 | 8/2006 | Nowlin et al. | |
| 7,103,344 B2 | 9/2006 | Menard | |
| 7,167,723 B2 | 1/2007 | Zhang | |
| 7,169,123 B2 | 1/2007 | Kadziauskas et al. | |
| 7,236,766 B2 | 6/2007 | Freeburg | |
| 7,236,809 B2 | 6/2007 | Fischedick et al. | |
| 7,242,765 B2 | 7/2007 | Hairston | |
| 7,244,240 B2 | 7/2007 | Nazarifar et al. | |
| 7,289,825 B2 | 10/2007 | Fors et al. | |
| 7,300,264 B2 | 11/2007 | Souza | |
| 7,316,664 B2 | 1/2008 | Kadziauskas et al. | |
| 7,336,976 B2 | 2/2008 | Ito | |
| 7,381,917 B2 | 6/2008 | Dacquay et al. | |
| 7,439,463 B2 | 10/2008 | Brenner et al. | |
| 7,465,285 B2 | 12/2008 | Hutchinson et al. | |
| 7,470,277 B2 | 12/2008 | Finlay et al. | |
| 7,526,038 B2 | 4/2009 | McNamara | |
| 7,591,639 B2 | 9/2009 | Kent | |
| 7,731,484 B2 | 6/2010 | Yamamoto et al. | |
| 7,776,006 B2 | 8/2010 | Childers et al. | |
| 7,811,255 B2 | 10/2010 | Boukhny et al. | |
| 7,883,521 B2 | 2/2011 | Rockley et al. | |
| 7,921,017 B2 | 4/2011 | Claus et al. | |

(56) References Cited

U.S. PATENT DOCUMENTS

| | | |
|---|---|---|
| 7,967,777 B2 | 6/2011 | Edwards et al. |
| 8,070,712 B2 | 12/2011 | Muri et al. |
| 8,075,468 B2 | 12/2011 | Min et al. |
| 2001/0023331 A1 | 9/2001 | Kanda et al. |
| 2001/0047166 A1* | 11/2001 | Wuchinich .................. 606/1 |
| 2001/0051788 A1 | 12/2001 | Paukovits et al. |
| 2002/0019215 A1 | 2/2002 | Romans |
| 2002/0019607 A1 | 2/2002 | Bui |
| 2002/0045887 A1 | 4/2002 | Dehoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2002/0183693 A1 | 12/2002 | Peterson et al. |
| 2003/0028091 A1 | 2/2003 | Simon et al. |
| 2003/0047434 A1 | 3/2003 | Hanson et al. |
| 2003/0050619 A1 | 3/2003 | Mooijman et al. |
| 2003/0073980 A1 | 4/2003 | Finlay et al. |
| 2003/0083016 A1 | 5/2003 | Evans et al. |
| 2003/0108429 A1 | 6/2003 | Angelini et al. |
| 2003/0125717 A1 | 7/2003 | Whitman |
| 2003/0224729 A1 | 12/2003 | Arnold |
| 2003/0226091 A1 | 12/2003 | Platenberg et al. |
| 2004/0035242 A1 | 2/2004 | Peterson et al. |
| 2004/0037724 A1 | 2/2004 | Haser et al. |
| 2004/0068300 A1* | 4/2004 | Kadziauskas et al. ........... 607/3 |
| 2004/0092922 A1 | 5/2004 | Kadziauskas et al. |
| 2004/0193182 A1 | 9/2004 | Yaguchi et al. |
| 2004/0212344 A1 | 10/2004 | Tamura et al. |
| 2004/0215127 A1 | 10/2004 | Kadziauskas et al. |
| 2004/0224641 A1 | 11/2004 | Sinn |
| 2004/0253129 A1 | 12/2004 | Sorensen et al. |
| 2005/0039567 A1 | 2/2005 | Peterson et al. |
| 2005/0054971 A1 | 3/2005 | Steen et al. |
| 2005/0069419 A1 | 3/2005 | Cull et al. |
| 2005/0070859 A1 | 3/2005 | Cull et al. |
| 2005/0070871 A1 | 3/2005 | Lawton et al. |
| 2005/0095153 A1 | 5/2005 | Demers et al. |
| 2005/0103607 A1 | 5/2005 | Mezhinsky |
| 2005/0109595 A1 | 5/2005 | Mezhinsky et al. |
| 2005/0118048 A1 | 6/2005 | Traxinger |
| 2005/0119679 A1* | 6/2005 | Rabiner ............ A61B 17/22012 606/159 |
| 2005/0130098 A1 | 6/2005 | Warner |
| 2005/0187513 A1 | 8/2005 | Rabiner et al. |
| 2005/0197131 A1 | 9/2005 | Ikegami |
| 2005/0209560 A1 | 9/2005 | Boukhny et al. |
| 2005/0236936 A1 | 10/2005 | Shiv et al. |
| 2005/0245888 A1 | 11/2005 | Cull |
| 2005/0261628 A1 | 11/2005 | Boukhny et al. |
| 2005/0267504 A1 | 12/2005 | Boukhny et al. |
| 2006/0035585 A1 | 2/2006 | Washiro |
| 2006/0036180 A1 | 2/2006 | Boukhny et al. |
| 2006/0041220 A1* | 2/2006 | Boukhny ........ A61B 17/320068 604/22 |
| 2006/0046659 A1 | 3/2006 | Haartsen et al. |
| 2006/0074405 A1 | 4/2006 | Malackowski et al. |
| 2006/0078448 A1 | 4/2006 | Holden |
| 2006/0114175 A1 | 6/2006 | Boukhny |
| 2006/0145540 A1 | 7/2006 | Mezhinsky |
| 2006/0219049 A1* | 10/2006 | Horvath et al. ................ 74/560 |
| 2006/0219962 A1 | 10/2006 | Dancs et al. |
| 2006/0224107 A1 | 10/2006 | Claus et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0066978 A1 | 3/2007 | Schafer et al. |
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0085611 A1 | 4/2007 | Gerry et al. |
| 2007/0107490 A1 | 5/2007 | Artsyukhovich et al. |
| 2007/0231205 A1 | 10/2007 | Williams et al. |
| 2007/0249941 A1 | 10/2007 | Salehi et al. |
| 2007/0249942 A1* | 10/2007 | Salehi et al. .................. 600/471 |
| 2008/0033342 A1 | 2/2008 | Staggs |
| 2008/0066542 A1 | 3/2008 | Gao |
| 2008/0067046 A1 | 3/2008 | Dacquay et al. |
| 2008/0082040 A1 | 4/2008 | Kubler et al. |
| 2008/0112828 A1 | 5/2008 | Muri et al. |
| 2008/0114289 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |
| 2008/0114312 A1 | 5/2008 | Muri et al. |
| 2008/0114372 A1 | 5/2008 | Edwards et al. |
| 2008/0114387 A1 | 5/2008 | Hertweck et al. |
| 2008/0125695 A1 | 5/2008 | Hopkins et al. |
| 2008/0125697 A1 | 5/2008 | Gao |
| 2008/0125698 A1 | 5/2008 | Gerg et al. |
| 2008/0129695 A1 | 6/2008 | Li |
| 2008/0146989 A1 | 6/2008 | Zacharias |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1 | 2/2009 | Rockley |
| 2009/0124974 A1 | 5/2009 | Crank et al. |
| 2009/0163853 A1 | 6/2009 | Cull et al. |
| 2010/0036256 A1 | 2/2010 | Boukhny et al. |
| 2010/0069825 A1 | 3/2010 | Raney |
| 2010/0069828 A1 | 3/2010 | Steen et al. |
| 2010/0185150 A1 | 7/2010 | Zacharias |
| 2010/0249693 A1 | 9/2010 | Links |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |
| 2012/0065580 A1 | 3/2012 | Gerg et al. |
| 2012/0083800 A1 | 4/2012 | Andersohn |
| 2013/0072853 A1 | 3/2013 | Wong et al. |
| 2013/0245543 A1 | 9/2013 | Gerg et al. |
| 2013/0289475 A1 | 10/2013 | Muri et al. |
| 2013/0303978 A1 | 11/2013 | Ross |

FOREIGN PATENT DOCUMENTS

| | | |
|---|---|---|
| EP | 56019 A1 | 7/1982 |
| EP | 424687 A1 | 5/1991 |
| EP | 0 619 993 | 10/1994 |
| EP | 0619993 A1 | 10/1994 |
| EP | 1010437 A1 | 6/2000 |
| EP | 1072285 A1 | 1/2001 |
| EP | 1113562 A1 | 7/2001 |
| EP | 1310267 A2 | 5/2003 |
| EP | 1464310 A1 | 10/2004 |
| EP | 1469440 A2 | 10/2004 |
| EP | 1550406 A2 | 7/2005 |
| EP | 1704839 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1867349 A1 | 12/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2352887 A | 2/2001 |
| GB | 2438679 A | 12/2007 |
| JP | S5724482 A | 2/1982 |
| JP | S58167333 A | 10/1983 |
| JP | 2008188110 A | 8/2008 |

(56) References Cited

FOREIGN PATENT DOCUMENTS

| | | | |
|---|---|---|---|
| WO | 9220310 | A1 | 11/1992 |
| WO | 9315777 | A2 | 8/1993 |
| WO | 9317729 | A1 | 9/1993 |
| WO | 9324082 | A1 | 12/1993 |
| WO | 9405346 | A1 | 3/1994 |
| WO | 9632144 | A1 | 10/1996 |
| WO | 9818507 | A1 | 5/1998 |
| WO | 9917818 | A1 | 4/1999 |
| WO | WO0000096 | A1 | 1/2000 |
| WO | 0070225 | A1 | 11/2000 |
| WO | 0122696 | A1 | 3/2001 |
| WO | 0228449 | A2 | 4/2002 |
| WO | 0234314 | A1 | 5/2002 |
| WO | 03102878 | A1 | 12/2003 |
| WO | 04096360 | A1 | 11/2004 |
| WO | 2004114180 | A1 | 12/2004 |
| WO | 05084728 | A2 | 9/2005 |
| WO | 2005/092047 | | 10/2005 |
| WO | 05092023 | A2 | 10/2005 |
| WO | 06101908 | A2 | 9/2006 |
| WO | 06125280 | A1 | 11/2006 |
| WO | 2007121144 | A1 | 10/2007 |
| WO | 2007143677 | A2 | 12/2007 |
| WO | 2007143797 | A1 | 12/2007 |
| WO | 2007149637 | A2 | 12/2007 |
| WO | 2008030872 | A1 | 3/2008 |
| WO | 2008060859 | | 5/2008 |
| WO | 2008060902 | A1 | 5/2008 |
| WO | 2008060995 | A1 | 5/2008 |
| WO | 2010054146 | A1 | 5/2010 |
| WO | 2010054225 | A2 | 5/2010 |
| WO | 2013142009 | A1 | 9/2013 |

OTHER PUBLICATIONS

English Human Translation of JP57024482 from Feb. 9, 1982.
European Search Report for Application No. EP10164058, dated Jun. 25, 2010, 2 pages.
European Search Report for Application No. EP13184138.9, dated Oct. 24, 2013, 7 pages.
Examination Report dated Mar. 28, 2012 for European Application No. EP09791072 filed Jul. 31, 2009, 3 pages.
International Search Report and Written Opinion for Application No. PCT/US2015/058655, dated Jan. 28, 2016, 13 pages.
International Search Report and Written Opinion, dated Nov. 2, 2009, and International Preliminary Report on Patentability, dated Feb. 1, 2011, for Application No. PCT/US2009/052466, 12 pages.
International Search Report for Application No. PCT/US07/083875, dated May 7, 2008, 4 pages.
International Search Report for Application No. PCT/US07/083880, dated May 30, 2008, 4 pages.
International Search Report for Application No. PCT/US07/084157, dated Apr. 1, 2008, 3 pages.
International Search Report for Application No. PCT/US07/084163, dated Apr. 1, 2008, 3 pages.
International Search Report for Application No. PCT/US08/064240, dated Oct. 29, 2008, 3 pages.
International Search Report for Application No. PCT/US08/071704, dated Nov. 26, 2008, 3 pages.
International Search Report for Application No. PCT/US08/072974, dated Feb. 23, 2009, 2 pages.
International Search Report for Application No. PCT/US2009/052473, dated Nov. 2, 2009, 3 pages.
Merritt R., et al., Wireless Nets Starting to link Medical Gear [online] 2004 [retrieved on Feb. 12, 2007]. Retrieved from the Internet: Feb. 12, 2007.
Phacoemulsification, [online] [retrieved on Jul. 1, 2009]. Retrieved from the Internet:, 2 pages.

* cited by examiner

SYSTEMS AND METHODS FOR TRANSVERSE PHACOEMULSIFICATION

FIELD OF THE INVENTION

The field of the invention relates to systems and methods for phacoemulsification, and more particularly to systems and methods for transverse phacoemulsification.

BACKGROUND OF THE INVENTION

A number of medically recognized techniques are utilized for cataractic lens removal based on, for example, phacoemulsification, mechanical cutting or destruction, laser treatments, water jet treatments, and so on.

The phacoemulsification method includes emulsifying, or liquefying, the cataractic lens with an ultrasonically driven needle before the lens is aspirated. A phacoemulsification system 5 known in the art is shown in FIG. 1. The system 5 generally includes a phacoemulsification handpiece 10 coupled to an irrigation source 30 and an aspiration pump 40. The handpiece 10 includes a distal tip 15 (shown within the anterior chamber of the patient's eye 1) that emits ultrasonic energy to emulsify the cataractic lens within the patient's eye 1. The handpiece 10 further includes an irrigation port 25 proximal to the distal tip 15, which is coupled to an irrigation source 30 via an irrigation line 35, and an aspiration port 20 at the distal tip 15, which is coupled to an aspiration pump 40 via an aspiration line 45. Concomitantly with the emulsification, fluid from the irrigation source 30, which is typically an elevated bottle of saline solution, is irrigated into the eye 1 via the irrigation line 35 and the irrigation port 25, and the irrigation fluid and emulsified cataractic lens material are aspirated from the eye 1 by the aspiration pump 40 via the aspiration port 20 and the aspiration line 45.

Turning to FIG. 2, a functional block diagram of a phacoemulsification system 100 known in the art is shown. The system 100 includes a control unit 102 and a handpiece 104 operably coupled together. The control unit 102 generally controls the operating parameters of the handpiece 104, e.g., the rate of aspiration A, rate of irrigation (or flow) F, and power P applied to the needle, and hence the eye E. The control unit 102 generally includes a microprocessor computer 110 which is operably connected to and controls the various other elements of the system 100. The control unit 102 may include an aspiration pump, such as a venturi (or vacuum-based pump) or a variable speed pump 112 (or a flow based or peristaltic pump) for providing a vacuum/aspiration source, which, in the case of a variable speed pump 112, can be controlled by a pump speed controller 116. The unit 102 further includes an ultrasonic power source 114 and an ultrasonic power level controller 118 for controlling the power P applied to the needle of the handpiece 104. A vacuum sensor 120 provides an input to the computer 110 representing the vacuum level on the output side of the pump 112. Venting may be provided by a vent 122. The system 100 may also include a phase detector 124 for providing an input to the computer 100 that represents the phase between a sine wave representation of the voltage applied to the handpiece 104 and the resultant current into the handpiece 104. Further disclosure about the phase detector 124 can be found in U.S. Pat. No. 7,169,123 to Kadziauskas et al., which is incorporated herein in its entirety by reference. The functional representation of the system 100 also includes a system bus 126 to enable the various elements to be operably in communication with each other.

Turning to FIG. 3, the cross-section along the longitudinal axis of a portion of a phacoemulsification handpiece 200 known in the art is shown. Generally, the handpiece 200 includes a needle 210, defining a lumen that is operatively coupled to the aspiration pump 40 (FIG. 1), forming an aspiration line 214. The proximal end of the needle 210 is coupled to a horn 250, which has its proximal end coupled to a set of piezoelectric crystals 280, shown as three rings. The horn 250, crystals 280, and a proximal portion of the needle 210 are enclosed within a handpiece casing 270 having an irrigation port coupled to an irrigation line 290 defining an irrigation pathway 295. The irrigation line 290 is coupled to the irrigation source 30 (FIG. 1). The horn 250 is typically an integrated metal, such as titanium, structure and often includes a rubber O ring 260 around the mid-section, just before the horn 250 tapers to fit with the needle 210 at the horn's 250 distal end. The O ring 260 snugly fits between the horn 250 and the casing 270. The O ring 260 seals the proximal portion of the horn 250 from the irrigation pathway 295. Thus, there is a channel of air defined between the horn 250 and the casing 270. Descriptions of handpieces known in the art are provided in U.S. Pat. No. 6,852,092 (to Kadziauskas et al.) and U.S. Pat. No. 5,843,109 (to Mehta et al.), which are hereby incorporated by reference in their entirety.

In preparation for operation, a sleeve 220 is typically added to the distal end of the handpiece 200, covering the proximal portion of the needle 210 (thus, exposing the distal tip of the needle), and the distal end of the irrigation pathway 295, thereby extending the pathway 295 and defining an irrigation port 222 just before the distal tip of the needle 210. The needle 210 and a portion of the sleeve 220 are then inserted through the cornea of the EYE to reach the cataractic lens.

During operation, the irrigation path 295, the eye's chamber and the aspiration line 214 form a fluidic circuit, where irrigation fluid enters the eye's chamber via the irrigation path 295, and is then aspirated through the aspiration line 214 along with other materials that the surgeon desires to aspirate out, such as the cataractic lens. If, however, the materials, such as the cataractic lens, are too hard and massive to be aspirated through the aspiration line 214, then the distal end of the needle 210 is ultrasonically vibrated and applied to the material to be emulsified into a size and state that can be successfully aspirated.

The needle 210 is ultrasonically vibrated by applying electric power to the piezoelectric crystals 280, which in turn, cause the horn 250 to ultrasonically vibrate, which in turn, ultrasonically vibrates the needle 210. The electric power is defined by a number of parameters, such as signal frequency and amplitude, and if the power is applied in pulses, then the parameters can further include pulse width, shape, size, duty cycle, amplitude, and so on. These parameters are controlled by the control unit 102 and example control of these parameters is described in U.S. Pat. No. 7,169,123 to Kadziauskas et al.

In a traditional phacoemulsification system 100, the applied electric power has a signal frequency that causes the crystal 280, horn 250, and needle 210 assembly to vibrate at a mechanically resonant frequency. This causes the needle 210 to vibrate in the longitudinal direction with a maximum range of motion, which many consider to be the state where the needle's cutting efficacy is at its maximum. However, there are a couple of known drawbacks. First, at this frequency, maximum power is applied to the needle that results in maximum heat introduced into the eye, which can cause undesirable burning of eye tissue. Second, the longitudinal motion can cause the material being emulsified to repel away from the needle, which is undesirable when the goal is to keep the material close to the needle to be aspirated (a quality often referred to as the needle's or handpiece's "followability").

To address the first issue, the power can be applied in pulses, where little or no power is applied in between the pulses, thus reducing the total amount of power and heat applied to the needle 210. To address the second issue, the power can be applied to the handpiece 200 to cause the needle 210 to vibrate in the transverse direction. An example of this approach is described in U.S. patent application Ser. No. 10/916,675 to Boukhny (U.S. Pub. No. 2006/0036180), which describes causing the needle 210 to vibrate in a torsional or twisting motion, which is a type of transverse motion. This application describes applying to the power to the needle 210 with a signal that alternates between two frequencies, one that causes longitudinal motion, and one that causes torsional motion with a particular type of horn having diagonal slits. This solution does provide for followability, but cutting efficacy leaves much for improvement.

Accordingly, an improved system and method for phacoemulsification is desirable.

SUMMARY OF THE INVENTION

The invention is generally directed to phacoemulsification systems and methods, and more particularly to systems and methods for providing transverse phacoemulsification.

In accordance with one embodiment, a phacoemulsification system is provided having a handpiece with a needle, wherein the phacoemulsification system is configured to vibrate the distal end of the needle in both an effective transverse direction and an effective longitudinal direction when power, having a single effective operating frequency is applied to the handpiece.

In accordance with other embodiments, phacoemulsification systems having handpieces with needles are provided, wherein the systems are configured to cause the needles to vibrate in a transverse direction.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than literally or precisely.

FIG. 10c-1 is a plot of the phase relationship and the impedance of a piezoelectric phacoemulsification handpiece in accordance with a preferred embodiment of the present invention.

DETAILED DESCRIPTION OF THE PREFERRED EMBODIMENTS

What are described below are preferred embodiments of phacoemulsification systems and handpieces and methods of use thereof.

Figure 1:
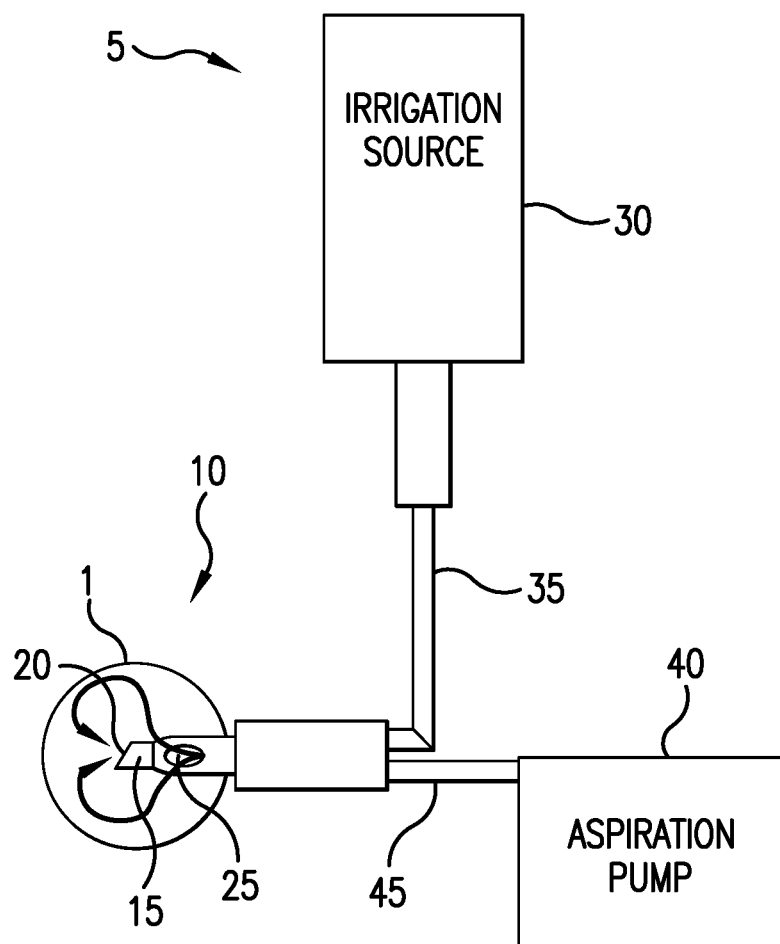
FIG. 1 is a diagram of a phacoemulsification system known in the art.
Figure 2:
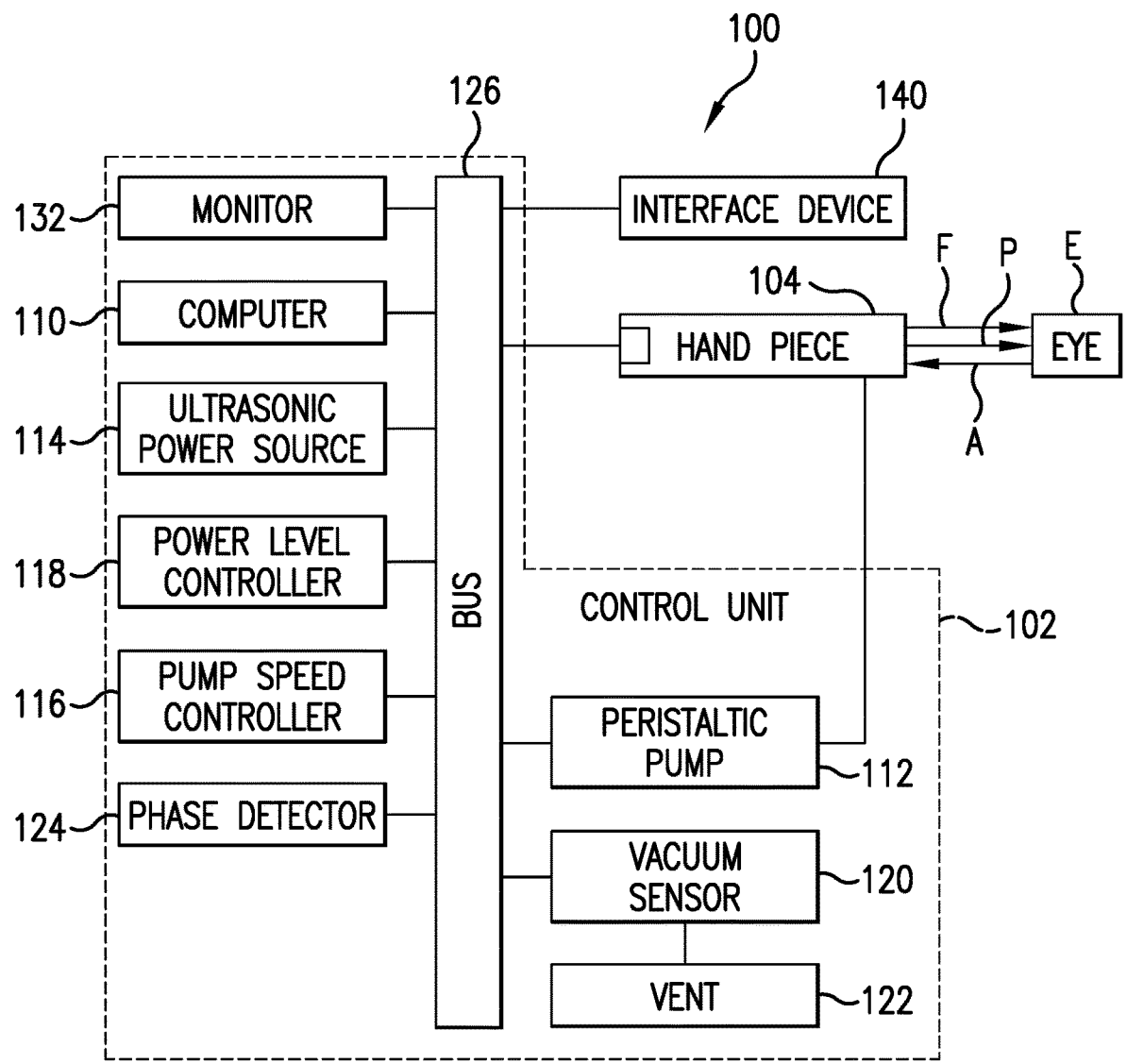
FIG. 2 is another diagram of a phacoemulsification system known in the art.
Figure 3:
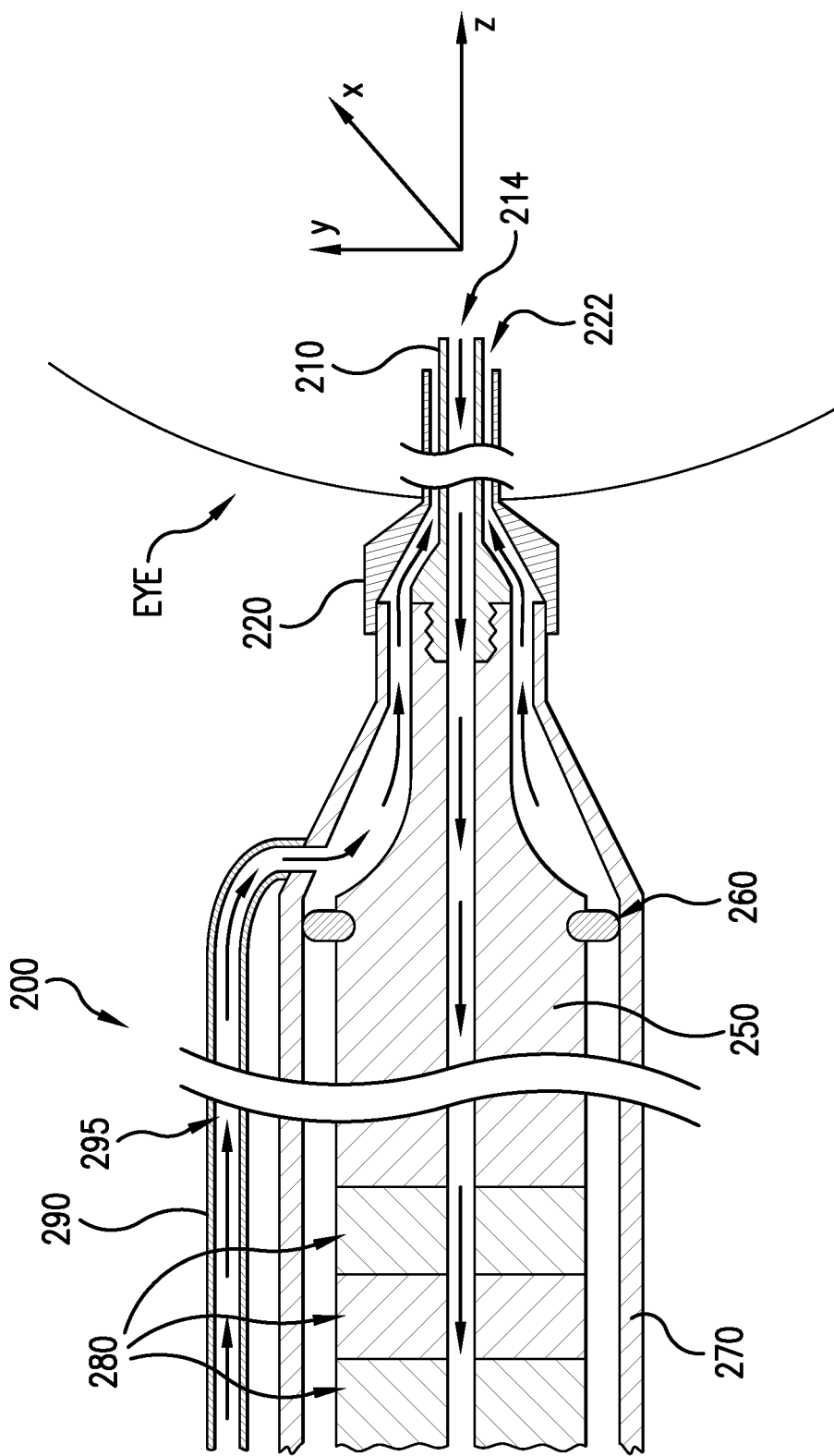
FIG. 3 is a diagram of a phacoemulsification handpiece known in the art.

Referring to FIG. 3, as mentioned above, there are existing phacoemulsification systems that enable the distal end of the phaco needle 210 to ultrasonically vibrate in a direction of the longitudinal axis of the handpiece 200, i.e., in the z direction, which provides optimum cutting efficacy but may cause less than optimum followability. There are also systems that enable the distal end of the phaco needle 210 to ultrasonic vibrate in a direction that is transverse of the longitudinal axis of the handpiece 200, in the x and/or y direction, which provides followability but less than optimum cutting efficacy. There further are systems that enable the distal end of the needle 210 to alternate between one type of direction and another by alternating between two different pulses of energy applied to the handpiece 200, each pulse having different signal frequencies. However, it may be desirable to enable the distal end of the needle 210 to move in both the transverse (x and/or y) and longitudinal (z) within a single pulse of energy or from power applied to the handpiece 200 having a single effective operating frequency, i.e., a frequency that may slightly shift due to conditions such as tuning, e.g., an effective operating frequency of 38 kHz may shift + or −500 Hz. A phacoemulsification system 100 that can achieve this gains the benefit of both followability and cutting efficacy.

There are two aspects of a phacoemulsification system that can individually or collectively enable both transverse and longitudinal ultrasonic vibration, (1) the structure of the handpiece 200 including the needle 210 and the horn 250, and (2) the computer readable instructions within the control unit 102. With regard to the structure of the handpiece 200, there are two aspects to the structure that can individually or collectively facilitate the desired outcome. First is the handpiece 200 center of mass relative to its longitudinal axis, and second is the structure of the handpiece 200 at the nodes and anti-nodes of the handpiece 200.

Figure 4A:
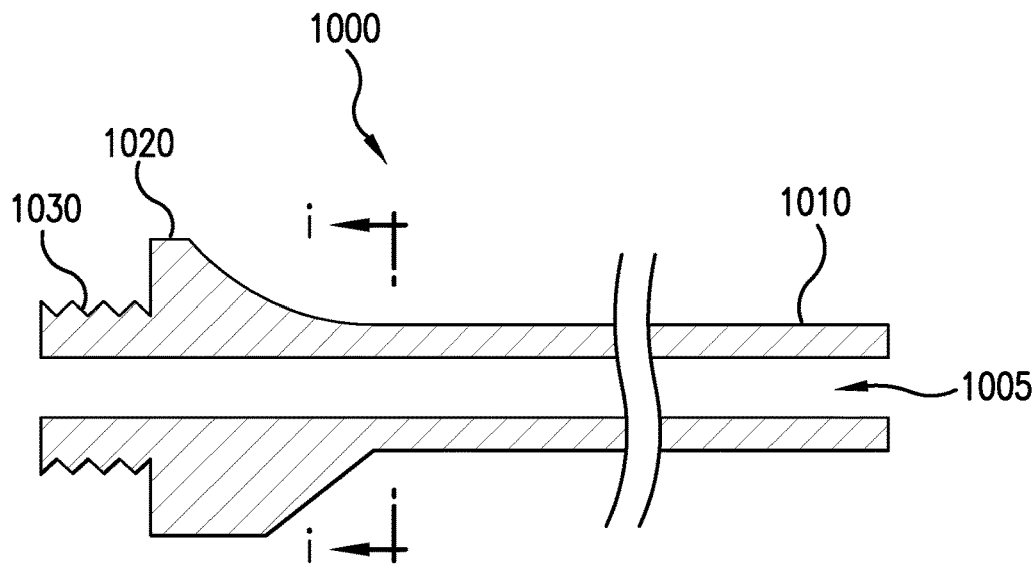
FIGS. 4a, b, c, d, and e are drawings of phacoemulsification needles in accordance with preferred embodiments of the present invention.

Turning to FIG. 4a, a needle 1000 is shown in accordance with a preferred embodiment of the invention. The needle 1000 is configured to be coupled to the distal end of an ultrasonically vibrated horn, e.g., 250. The needle 1000 includes a distal tip 1010 defining a lumen 1005 for aspiration, a needle base 1020 proximal to the tip 1010, and a needle interface/adapter 1030 to couple the needle with the horn, e.g., 250. Conventional needles, e.g., 210, have a center of mass located on its longitudinal axis. The needle 1000 has a structure with a center of mass that is off from the longitudinal axis. This is achieved by having an asymmetric needle base 1020.

Figure 4B:
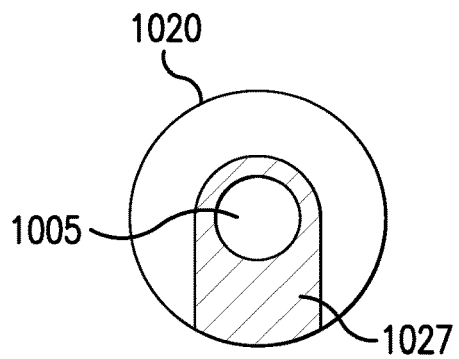
Figure 4C:
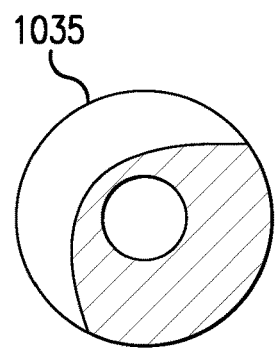
Figure 4D:
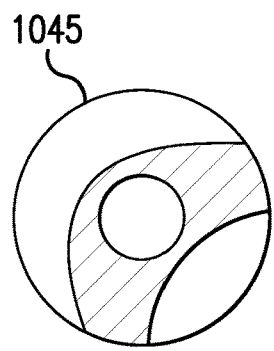
Figure 4E:
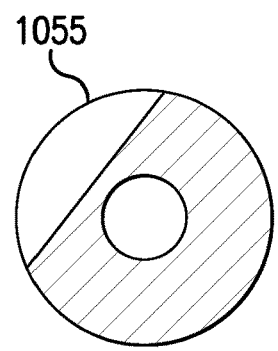

Turning to FIG. 4b, a cross-sectional view of the needle 1000 is shown from the direction i, as indicated in FIG. 4a. The needle base 1020 has a portion of mass etched out, leaving a portion 1027, creating an asymmetric configuration. Alternative needle base configurations 1035, 1045, and 1055 are shown in FIGS. 4c, 4d, and 4e respectively. FIG. 4e showing an asymmetric needle base 1055 having a single side substantially carved out or flattened.

Figure 5A:
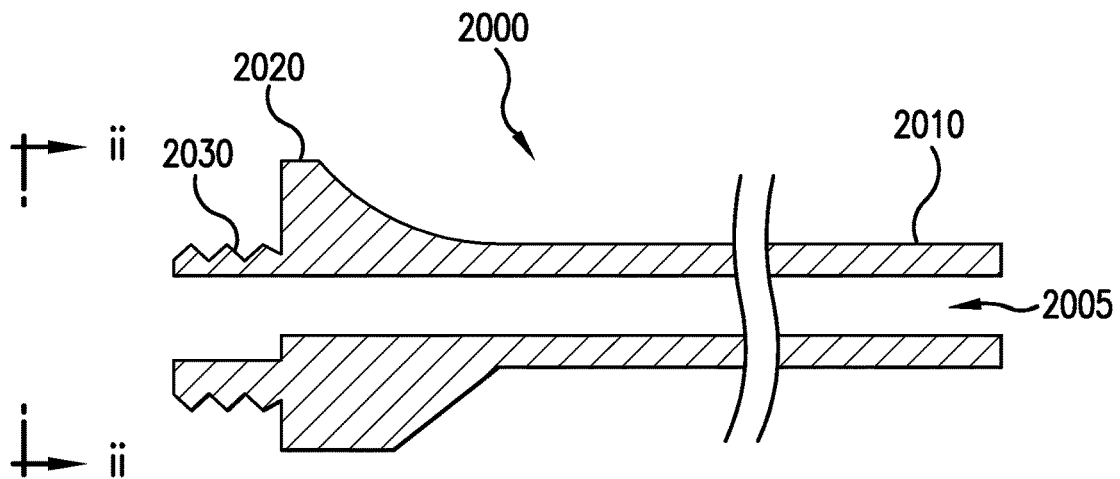
FIGS. 5a and b are drawings of phacoemulsification needles in accordance with preferred embodiments of the present invention.
Figure 5B:
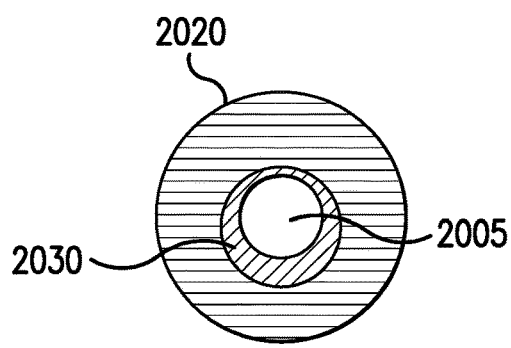

Turning to FIG. 5a, another needle 2000, having a distal tip 2010, base 2020, and needle interface/adapter 2030, is shown with a center of mass off from the longitudinal axis. In the alternative, or in addition to, the asymmetric base 1020, the needle 2000 can have an off-center interface/adapter 2030. Turning to FIG. 5b, a cross-sectional view of the needle 200 is shown from the direction ii, as indicated in FIG. 5a. The interface/adapter 2030 is concentric with but off-center with the aspiration line 2005.

Figure 6:
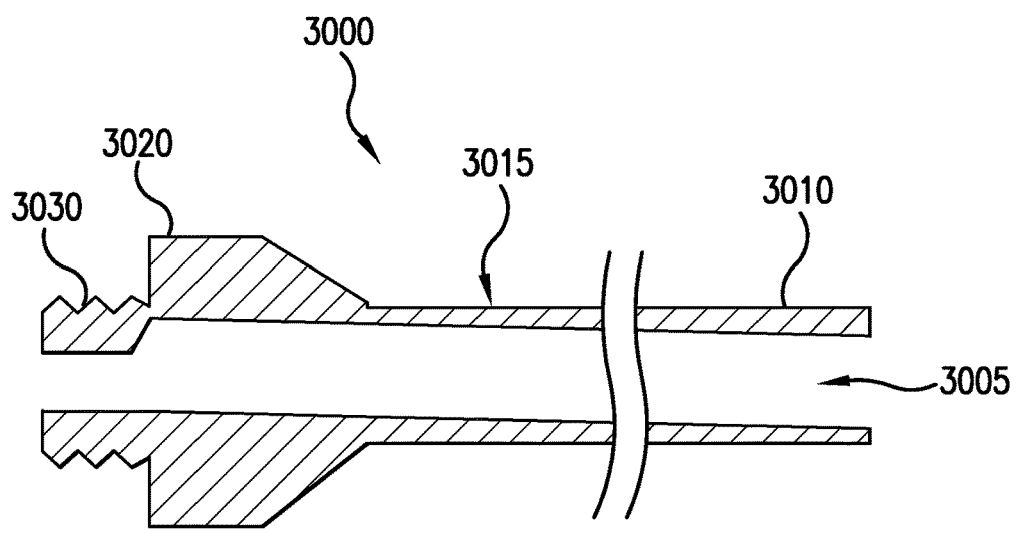
FIG. 6 is a drawing of a phacoemulsification needle in accordance with a preferred embodiment of the present invention.

Turning to FIG. 6, another needle 3000, having a distal tip 3010, base 3020, and needle interface/adapter 3030, is shown with a center of mass off from the longitudinal axis. In addition to, or in the alternative, to the embodiments described above, though the outside surface 3015 of the needle 3000 is parallel with the longitudinal axis, the aspiration line 3005 is configured to be angled with respect to the needle's 3000 longitudinal axis.

Figure 7:
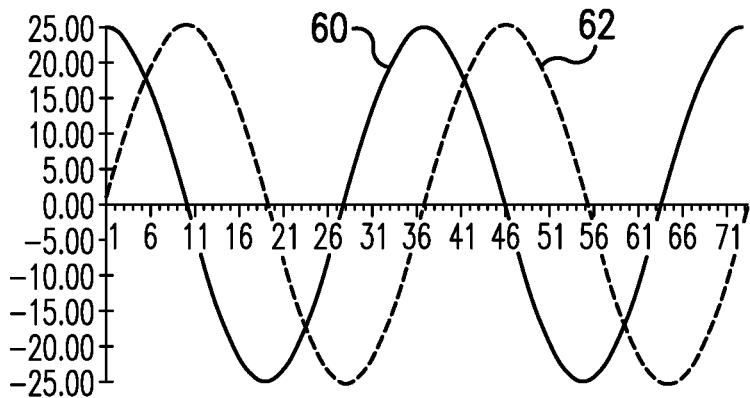
FIG. 7 is a plot of the 90-degree phase shift between the sine wave representation of the voltage applied to a piezoelectric phacoemulsification handpiece and the resultant current into the handpiece.

As mentioned above, the control unit 102 can also contribute to providing transverse and longitudinal motion of the needle, e.g., 210, 1000, 2000, and 3000. The typical range of frequencies used for a phacoemulsification system 100 is between about 30 kHz and about 50 kHz. The frequency used often depends upon the structure of the handpiece 200 and many systems 100 are designed to apply a frequency corresponding to the resonant frequency of the handpiece 200, which, as explained above, causes the needle 210 to vibrate in a maximum longitudinal range of motion. When the frequency applied to the handpiece is significantly higher, or lower than resonancy, it responds electrically as a capacitor. The representation of this dynamic state is shown in FIG. 7 in which curve 60 (solid line) represents a sine wave corresponding to handpiece 30 current and curve 62 (broken line) represents a sine wave corresponding to handpiece 30 voltage.

Figure 8A:
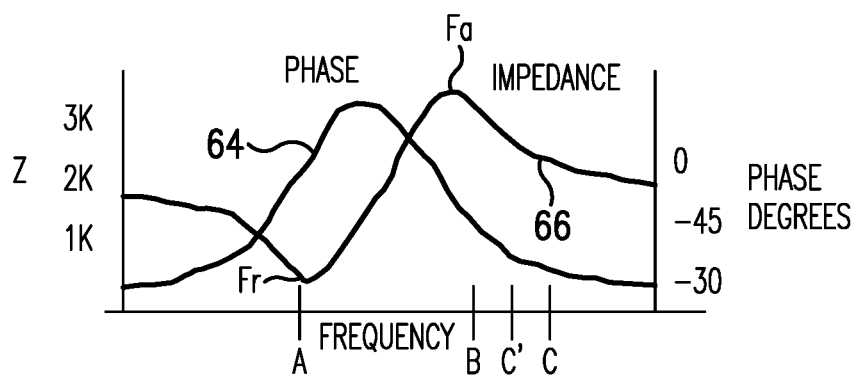
FIG. 8a is a plot of the phase relationship and the impedance of a piezoelectric phacoemulsification handpiece.

Turning to FIG. 8, as is known in the art, the impedance of the typical phacoemulsification handpiece 200 varies with frequency, i.e., it is reactive. The dependence of typical handpiece 30 phase and impedance as a function of frequency is shown in FIG. 8a in which curve 64 represents the phase difference between current and voltage of the handpieces function frequency and curve 66 shows the change in impedance of the handpiece as a function of frequency. The impedance exhibits a low at "Fr" and a high "Fa" for a typical range of frequencies.

Figure 8B:
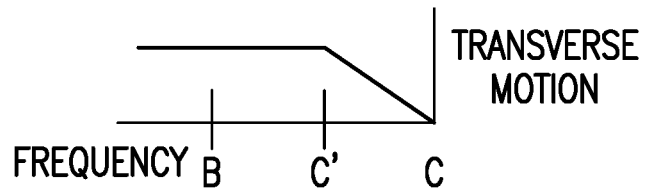
FIG. 8b is a plot of the range of transverse motion with respect to frequency.

Some conventional phacoemulsification systems 100 apply power to the handpiece 200 at Fr (point A) which generally causes the needle 210 to vibrate in the longitudinal direction. In one approach, particularly with the needles described above, 1000, 2000, and 3000, it may be desirable to move the signal frequency of the power applied to the handpiece 200 up to point C. The frequency applied at point C causes the needle, e.g., 210, 1000, 2000, and 3000, to effectively vibrate both in the z direction as well as the x and/or y direction (i.e., sustained and substantial vibration as opposed to transitional vibration, such as vibration that could occur when the power signal shifts from one frequency causing longitudinal movement to a second frequency causing transversal movement, or incidental vibration, such as any minimal transversal vibration when the needle is predominantly vibrating in the longitudinal direction). It was determined that the ratio of range of motion between the longitudinal and the transverse direction is approximately 1:1 with about 0.75 to 1 mil range of motion in both directions, which provides the operation of the needle with effective followability and cutting efficacy. However, power usage at this frequency is less than a Watt, so the longitudinal range of motion is effective but limited, and thus, so is the cutting efficacy. To increase the cutting efficacy, the impedance can be increased, which can be achieved by moving the operating frequency down to point B, where the longitudinal range of motion increases, thereby increasing cutting efficacy. Turning to FIG. 8b, the amount of transverse motion is graphed relative to the frequency from point C to point B. This shows that the range of transverse motion increases as the frequency decreases up to a certain point before reaching point B, and then the transverse motion range saturates at a point between point B and point C, C'. For the standard WhiteStar™ handpiece, the Fr is approximately 36.6 kHz, Fa is approximately 37.1 kHz, point B is approximately 37.2 kHz, and point C is approximately 37.8 kHz.

Figure 9A:
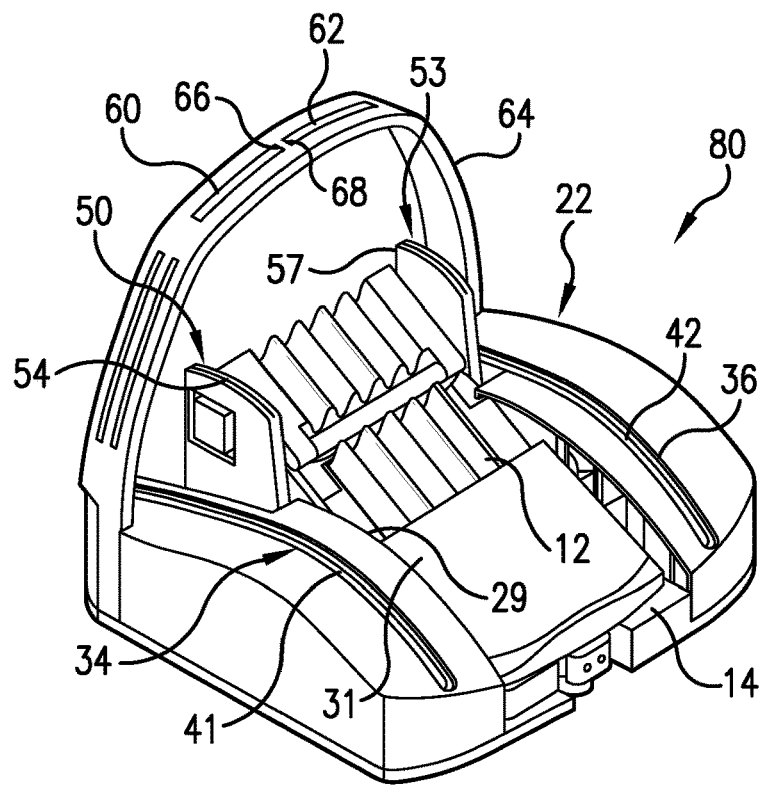
FIGS. 9a and b are drawings of phacoemulsification footswitches.

A surgeon can control these various types of vibrations by using a footswitch that is coupled with the control unit 102. With reference to FIG. 9a there is shown apparatus 80 for controlling a handpiece 200 during surgery which includes a foot pedal 12 pivotally mounted to a base 14 for enabling a depression thereof in order to provide control signals for handpiece 200 operation. A foot pedal 12 may be similar or identical to known foot pedals such as, for example set forth in U.S. Pat. No. 5,983,749, issued Nov. 16, 1999 for Duel Position Foot Pedal for Ophthalmic Surgery apparatus or U.S. patent application Ser. No. 09/140,874 filed Aug. 29, 1998 for Back Flip Medical Foot Pedal.

Support surfaces in the form of shrouds 29, 22 may be provided and disposed adjacently foot pedal 12 on opposite sides 26, 31 at a position enabling access thereto by a user's foot (not shown). The first and second foot activated ribbons switches 34, 36 to are disposed on the surfaces 29, 22 in a conventional manner such as gluing or the like, and have a length extending along the surfaces 29, 22 which is sufficient to enable actuation of the ribbon switches 34, 36 by a user's foot (not shown) without visual operation thereof by the user (not shown). More detail about this footswitch 80 can be found in U.S. Pat. No. 6,452,123 to Jerry Chen, which is hereby incorporated in its entirety.

As can be appreciated by one of ordinary skill in the art, the footswitch 80 can be configured to control the longitudinal vibration of the distal end of the needle 210, 1000, 2000, and 3000 with the pitch movement of the footpedal 52 via the control unit 102 by associating the pitch movement of the foot pedal 12 with the power level and transverse vibration of the distal end of the needle 210, 1000, 2000, and 3000 with either ribbon switches 36, 36.

Figure 9B:
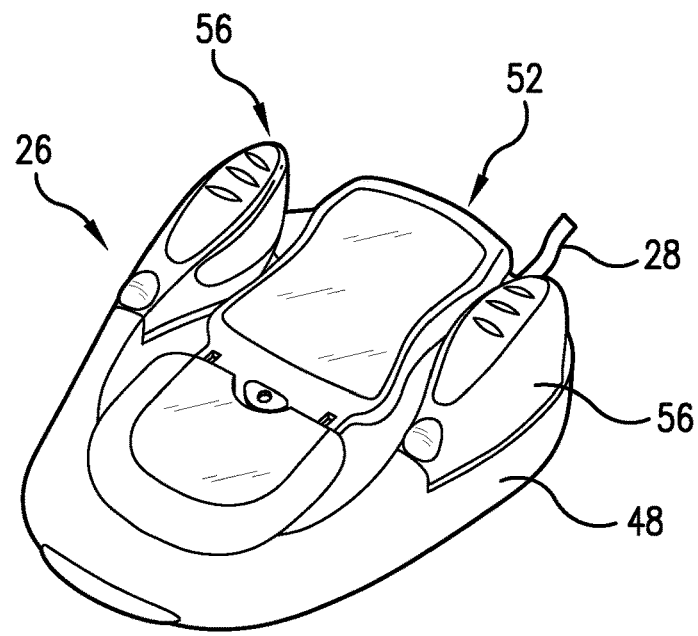

Turning to FIG. 9b, another footswitch 26 in accordance with a preferred embodiment is shown. The footswitch 26 includes a base 48, two side switches 56, a data and/or power cable 28 to couple the footswitch 26 to the control unit 102 (a wireless interface known in the art, such as Bluetooth, can also be employed), and a footpedal 52 that allows for both pitch and yaw movement. As can be appreciated by one of ordinary skill in the art, the footswitch 26 can be configured to control the longitudinal vibration of the distal end of the needle 210, 1000, 2000, and 3000 with the pitch movement of the footpedal 52 via the control unit 102 by associating the pitch movement of the footpedal 52 with the power level and transverse vibration of the distal end of the needle 210, 1000, 2000, and 3000 with either the yaw movement of the footpedal 52 or the side switches 56. For example, the yaw movement of the footpedal 52 or the side switches 56 can be associated with the frequency of the power applied to the handpiece 200. In a further example, the yaw movement of the footpedal 52 can be associated with the range of frequencies between point B and point C in FIG. 8b. In addition, the side switches 56 can be used to allow the surgeon to toggle between using point A, where cutting efficacy is at its optimum, and using a frequency between point B and point C, where transverse motion can be controlled by the yaw movement of the footpedal 52.

Figure 10A:
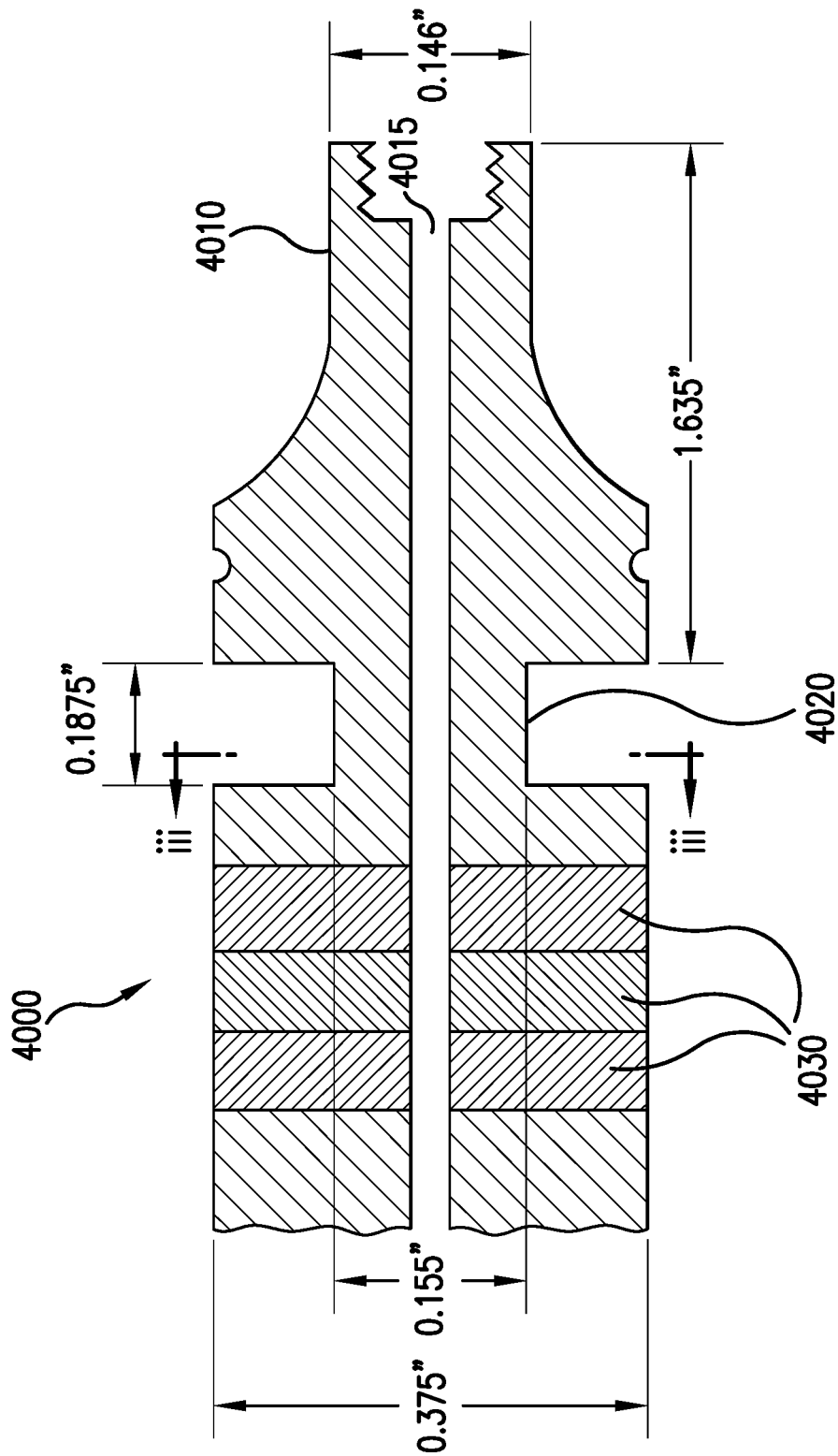
FIGS. 10a, b, and c are drawings of phacoemulsification horns in accordance with preferred embodiments of the present invention.

In addition to, or in the alternative to, the needle structure, e.g., 210, 1000, 2000, and 3000, transverse and simultaneous transverse/longitudinal vibrations can further be achieved through the structure of the horn 250 and piezocrystal stack 280 configuration. Generally, it may be desirable to configure the horn 250 to have an asymmetric mass or a center of mass off from the horn's 250 longitudinal axis. Turning to FIG. 10a, a horn 4000 in accordance with a preferred embodiment is shown. The horn 4000 includes a distal end 4010, configured to engage an ultrasonic needle, e.g., 210, 1000, 2000, and 3000. The distal end 4010 of the horn 4000 has a diameter of approximately 0.146". The horn 4000 defines a lumen 4015, which functions as an aspiration line. The proximal section of the horn 4000, which has a diameter of about 0.375", includes a notch 4020 having a length of approximately 0.1875" and a core width of approximately 0.155". The distance between the distal end 4010 of the horn 4000 and the distal end of the notch 4020 is approximately 1.635". The proximal section of the horn 4000 is coupled to a stack of piezoelectric crystal rings 4030.

Figure 10B:
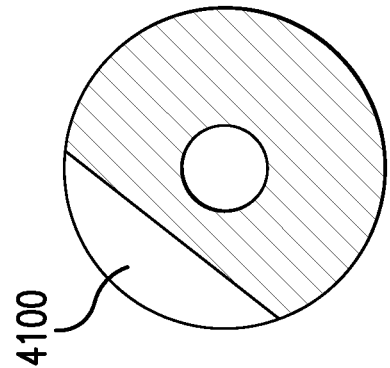
Figure 10C:
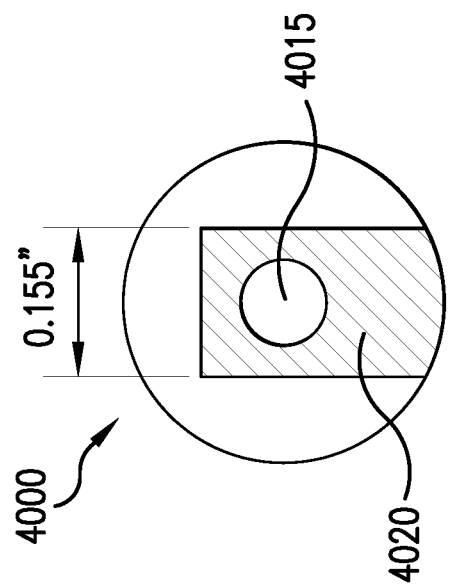
Figures 1, 10C:
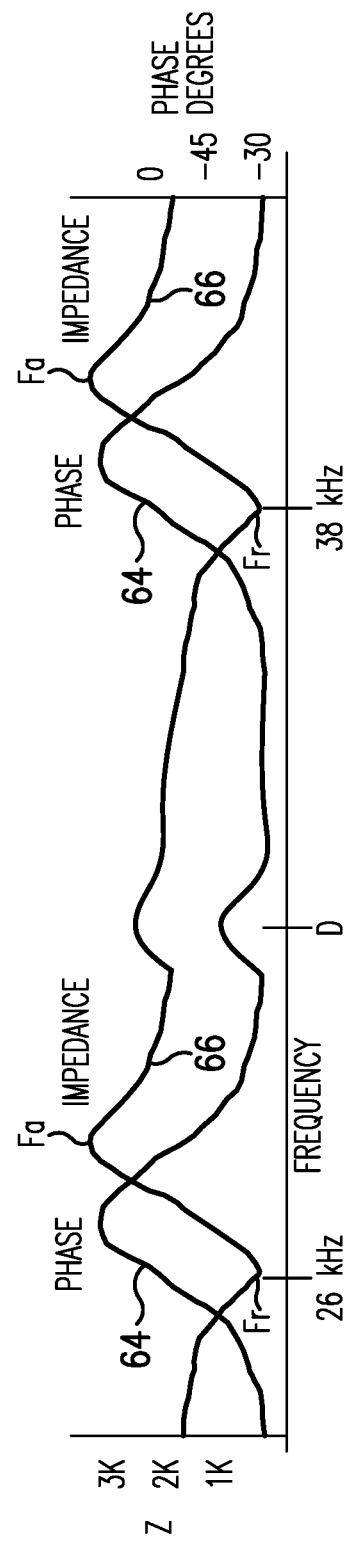

Turning to FIG. 10b, a cross-section of the horn 4000 taken along direction line iii is shown. In one embodiment, the notch 4020 is created by carving out three sides of the horn 4000 at the location of the notch 4020. In another embodiment, shown in FIG. 10c, a horn 4100 is shown with a notch defined by only one side. Multiple notches can be created. Thus, FIGS. 10b and 10c illustrate cross sections of horns 4000 and 4100, respectively, formed with an absence of material on a periphery of a portion of the horn such that the periphery of the portion of the horn has an irregular and noncircular shape and the center of mass is offset from the longitudinal axis of the horn.

A profile of this horn's 4000 characteristics along a frequency spectrum is shown in FIG. 10d. Phacoemulsification handpieces 200 typically have multiple resonant frequencies. The impedance/phase profile shown in FIG. 8b is for the traditional operating frequency, e.g., in the range of 30 to 40 kHz. A similar profile can be also shown at other resonant frequencies, e.g., in the range of 20 to 30 kHz. With horn 4000, it was determined that at 38 kHz, a maximum range of longitudinal vibration is provided at the needle 210 distal tip. When the operating frequency, however, is dropped down to a lower resonant frequency, e.g., 26 kHz, both effective (sustained and substantial) transverse and effective longitudinal ranges of motion are provided at the needle 210 distal tip. Furthermore, depending on the shape and location of the notch 4020 formed on the horn 4000, an additional transversal node can be created on the frequency spectrum, e.g., point D (which was determined to be about 28 kHz with horn 4000, where the operating frequency at point D causes the needle 210 distal tip to vibrate predominantly in the transverse direction, e.g., x and/or y direction. The location of the transversal node, point D, relative to the resonant frequencies, is dependent upon the horn configuration and material, and can even be used to coincide with a resonant frequency, thereby enhancing transversal motion at that frequency.

Figure 11:
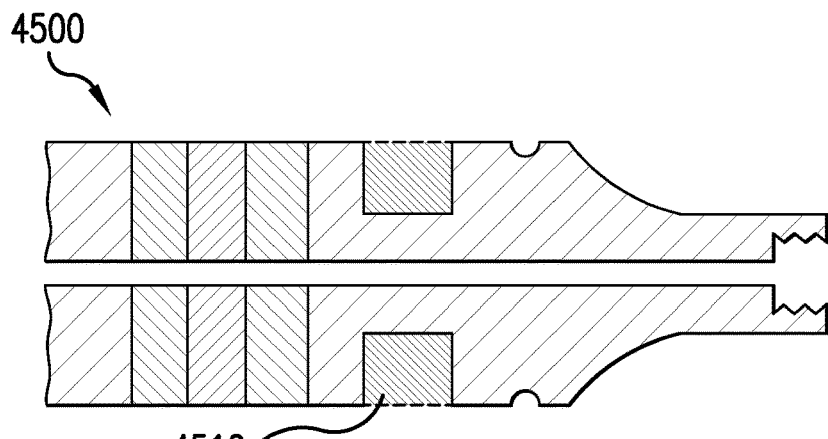
FIG. 11 is a drawing of a phacoemulsification horn.

The following are other horn configurations that can provide the profile discussed above and shown in FIG. 10c. Turning to FIG. 11, another horn 4500 configuration is shown having a notch 4510, wherein the notch 4510 is filled with an acoustic material known in the art, such as silicon.

Figure 12:
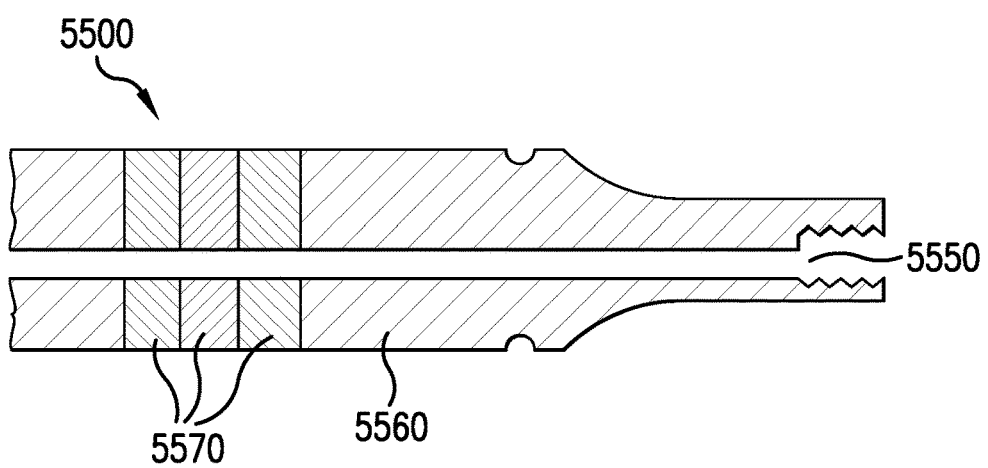
FIG. 12 is a drawing of a phacoemulsification horn.

Turning to FIG. 12, another horn assembly 5500 is shown having the horn body 5560 and piezocrystal crystal stack 5570 define a lumen 5550 that is off from the horn's 5500 central longitudinal axis.

Figure 13:
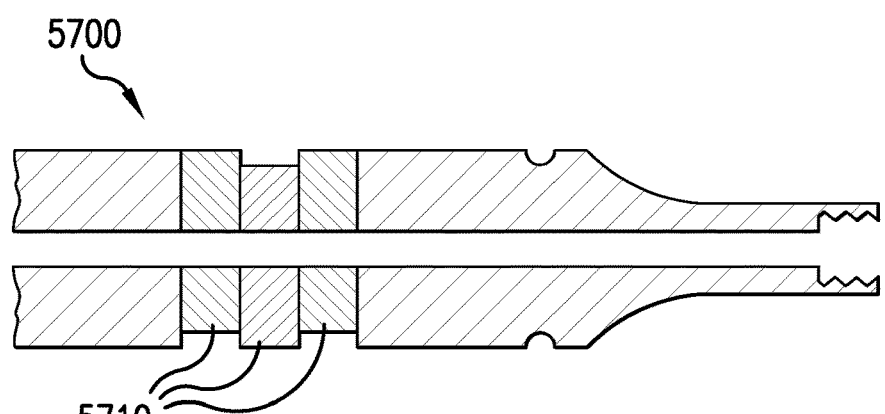
FIG. 13 is a drawing of a phacoemulsification horn.

Turning to FIG. 13, another horn assembly 5700 is shown having the piezocrystal stacks 5710 with staggered slightly.

Accordingly, with a phacoemulsification handpiece 200 constructed with a horn 4000, 4500, 5500, 5700, the control unit 102 can be configured to provide three types of vibration for the ultrasonic needle, 210, 1000, 2000, or 3000, (1) longitudinal, (2) transversal, and (3) a hybrid with effective transversal and effective longitudinal motion. Furthermore, the control unit 102 can also apply variations of these modes in pulses, as described in U.S. Pat. No. 7,169,123, wherein a single pulse of energy with a single operating frequency applied to the needle can cause distal end of the needle 210, 1000, 2000 or 3000 to vibrate in either the longitudinal direction, transversal direction, or both, and further wherein different pulses causing different types of vibration that can be juxtaposed and controlled by the surgeon, e.g., the interface device 140 such as a computer or the footswitch 26, 80. The pulses described above can further be shaped, as described in U.S. patent application Ser. No. 10/387,335 to Kadziauskas et al., which is hereby incorporated by reference in its entirety.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention may appropriately be performed using different or additional process actions, or a different combination or ordering of process actions. For example, this invention is particularly suited for applications involving medical systems, but can be used beyond medical systems in general. As a further example, each feature of one embodiment can be mixed and matched with other features shown in other embodiments. Additionally and obviously, features may be added or subtracted as desired. Accordingly, the invention is not to be restricted except in light of the attached claims and their equivalents.

What is claimed is:

1. A phacoemulsification system, comprising:
   a phacoemulsification handpiece having a needle and a horn, the needle having a distal end and at least one notch carved out of a side of an outer surface of the horn, wherein the at least one notch moves a center of mass of the horn offset from a central longitudinal axis of the horn and the outer surface of the horn does not intersect with the longitudinal axis of the horn,
   wherein the phacoemulsification handpiece is configured to vibrate the distal end of the needle in both an effective transverse direction and an effective longitudinal direction when power, having a single effective operating frequency, is applied to the phacoemulsification handpiece; and
   a control unit operatively coupled to the phacoemulsification handpiece and configured to provide power to the phacoemulsification handpiece.

2. The phacoemulsification system of claim 1, wherein the control unit is configured to provide power to the phacoemulsification handpiece so that the distal end of the needle vibrates substantially simultaneously both in the effective longitudinal direction and the effective transverse direction.

3. The phacoemulsification system of claim 1, wherein the control unit is configured to provide a single pulse of power to the phacoemulsification handpiece.

4. The phacoemulsification system of claim 1, wherein the handpiece further comprises one or more piezoelectric crystals.

5. The phacoemulsification system of claim 4, wherein the one or more piezoelectric crystals are stacked along the longitudinal axis of the horn and define a lumen formed offset from the longitudinal axis of the horn.

6. The phacoemulsification system of claim 1, wherein the needle further comprises an asymmetrically formed base formed with a portion of mass etched out so that the center of mass of the needle is offset from a longitudinal axis of the needle.

7. The phacoemulsification system of claim 1, wherein the outer surface of the horn extends radially away from the longitudinal axis of the horn.

8. The phacoemulsification system of claim 1, wherein the outer surface of the horn extends radially away from a lumen defined within the horn.

9. The phacoemulsification system of claim 1, wherein the notch is created by carving out three sides of the horn.

10. The phacoemulsification system of claim 1, wherein the notch extends from the outside surface of the horn towards the longitudinal axis of the horn.

11. The phacoemulsification system of claim 10, wherein the notch does not breach the longitudinal axis of the horn.

12. A phacoemulsification system, comprising:
    a phacoemulsification handpiece having a needle and a horn assembly, wherein the horn assembly comprises a horn and one or more piezoelectric crystals and the horn assembly having at least one notch carved out of a side of an outer surface of the horn wherein the at least one notch moves a center of mass of the horn offset from a central longitudinal axis of the horn and the outer surface of the horn does not intersect with the longitudinal axis of the horn,
    wherein the phacoemulsification handpiece is configured to vibrate a distal end of the needle in both an effective transverse direction and an effective longitudinal direction when power, having a single effective operating frequency, is applied to the phacoemulsification handpiece; and
    a control unit operatively coupled to the phacoemulsification handpiece and configured to provide power to the phacoemulsification handpiece.

13. The phacoemulsification system of claim 12, wherein at least one of the piezoelectric crystals has a mass offset from the longitudinal axis of the horn.

14. The phacoemulsification system of claim 13, wherein a body of the at least one of the piezoelectric crystals defines a lumen that is off from the longitudinal axis of the horn.

15. The phacoemulsification system of claim 12, wherein the control unit is configured to provide power to the phacoemulsification handpiece so that the distal end of the needle vibrates substantially simultaneously in both the effective longitudinal direction and the effective transverse direction.

16. The phacoemulsification system of claim 12, wherein the control unit is configured to provide a single pulse of power to the phacoemulsification handpiece.

17. A phacoemulsification system, comprising:
    a phacoemulsification handpiece having a horn with at least one notch carved out of a side of an outer surface of the horn, wherein the at least one notch moves a center of mass of the horn offset from a central longitudinal axis of the horn and the outer surface of the horn does not intersect with the longitudinal axis of the horn;
    one or more piezoelectric crystals;
    a needle having an adapter configured to couple the needle with the horn, the adapter having a center of mass off from a longitudinal axis of the needle,
    wherein the phacoemulsification handpiece is configured to vibrate a distal end of the needle in both an effective transverse direction and an effective longitudinal direction when power, having a single effective operating frequency, is applied to the phacoemulsification handpiece; and
    a control unit operatively coupled to the phacoemulsification handpiece and configured to provide power to the phacoemulsification handpiece.

18. The phacoemulsification system of claim 17, wherein the needle comprises an aspiration line wherein the adapter is formed concentric with but offcenter with the aspiration line.

19. The phacoemulsification system of claim 17, wherein the control unit is configured to provide power to the phacoemulsification handpiece so that the distal end of the needle vibrates substantially simultaneously in both the effective longitudinal direction and the effective transverse direction.

20. The phacoemulsification system of claim 17, wherein the control unit is configured to provide a single pulse of power to the phacoemulsification handpiece.

21. A phacoemulsification system, comprising:
    a phacoemulsification handpiece having a horn with at least one notch carved out of a side of an outer surface of the horn, wherein the at least one notch moves a center of mass of the horn offset from a central longitudinal axis of the horn and the outer surface of the horn does not intersect with the longitudinal axis of the horn;
    one or more piezoelectric crystals;

a needle having an asymmetrical needle base formed with a center of mass off from a longitudinal axis of the needle, wherein the phacoemulsification handpiece is configured to vibrate a distal end of the needle in both an effective transverse direction and an effective longitudinal direction when power, having a single effective operating frequency, is applied to the phacoemulsification handpiece; and a control unit operatively coupled to the phacoemulsification handpiece and configured to provide power to the phacoemulsification handpiece.

22. The phacoemulsification system of claim 21, wherein the asymmetric needle base has a portion of mass etched out on a portion of a periphery of the needle base.

23. The phacoemulsification system of claim 21, wherein the control unit is configured to provide power to the phacoemulsification handpiece so that the distal end of the needle substantially simultaneously vibrates in both the effective longitudinal direction and the effective transverse direction.

24. The phacoemulsification system of claim 21, wherein the control unit is configured to provide a single pulse of power to the phacoemulsification handpiece.

25. A phacoemulsification system, comprising:
a phacoemulsification handpiece having a needle, a horn with at least one notch carved out of a side of an outer surface of the horn, wherein the at least one notch moves a center of mass of the horn offset from a central longitudinal axis of the horn and the outer surface of the horn does not intersect with the longitudinal axis of the horn, and a piezoelectric crystal stack,
wherein the phacoemulsification handpiece is configured to vibrate a distal end of the needle in both an effective transverse direction and an effective longitudinal direction when power, having a single effective operating frequency, is applied to the phacoemulsification handpiece; and
a control unit operatively coupled to the phacoemulsification handpiece and configured to provide power to the phacoemulsification handpiece,
wherein the control unit is configured to provide a single pulse of power to the phacoemulsification handpiece so that the distal end of the needle substantially simultaneously vibrates in both the effective longitudinal direction and the effective transverse direction.

26. A phacoemulsification system, comprising:
a phacoemulsification handpiece having a needle, a horn with at least one notch carved out of a side of an outer surface of the horn, wherein the at least one notch moves a center of mass of the horn offset from a central longitudinal axis of the horn and the outer surface of the horn does not intersect with the longitudinal axis of the horn, and a piezoelectric crystal stack,
wherein the phacoemulsification handpiece is configured to vibrate a distal end of the needle in both an effective transverse direction and an effective longitudinal direction when power, having a single effective operating frequency, is applied to the phacoemulsification handpiece; and
a control unit operatively coupled to the phacoemulsification handpiece and configured to provide power to the phacoemulsification handpiece,
wherein the control unit is configured to provide power at the single effective operating frequency to the phacoemulsification handpiece so that the distal end of the needle substantially simultaneously vibrates in both the effective longitudinal direction and the effective transverse direction.

* * * * *